US00PP36078P2

(12) United States Plant Patent
Bédard

(10) Patent No.: US PP36,078 P2
(45) Date of Patent: Aug. 27, 2024

(54) SHRUB ROSE PLANT NAMED 'WEKblufstow'

(50) Latin Name: *Rosa hybrida*
Varietal Denomination: WEKblufstow

(71) Applicant: Early Morning LLC, Lawrenceburg, IN (US)

(72) Inventor: Christian Bédard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/533,666

(22) Filed: Dec. 8, 2023

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./101, 102
See application file for complete search history.

(56) References Cited

U.S. PATENT DOCUMENTS

PP20,325 P3 9/2009 James
PP23,158 P2 11/2012 Orard

OTHER PUBLICATIONS

Bedard, C., "Grandiflora Rose Plant Named "Weksecjuc"," U.S. Appl. No. 18/390,244, filed Dec. 20, 2023, 10 pages.
Carruth, T., "Grandiflora Rose Plant Named "Wekalmylcas"," U.S. Appl. No. 18/540,248, filed Dec. 14, 2023, 11 pages.
Carruth, T., "Hybrid Tea Rose Plant Named "Wekmotonton"," U.S. Appl. No. 18/541,817, filed Dec. 15, 2023, 11 pages.
Make Me Blush TM, "Weeks Roses," 2024 Wholesale Rose Catalog, 2024, 100 pages.

*Primary Examiner* — Karen M Redden
(74) *Attorney, Agent, or Firm* — McKee, Voorhees & Sease, PLC

(57) ABSTRACT

A new variety of Shrub rose suitable for garden decoration, having flowers of magenta-purple with white reverse coloration.

1 Drawing Sheet

Classification: The present invention relates to a new *Rosa hybrida* plant.

Variety denomination: The new plant has the varietal denomination 'WEKblufstow'.

BACKGROUND OF THE INVENTION

This invention relates to a new and distinct variety of Shrub Rose. It has as its seed parent the variety known as 'PEJamblu' (U.S. Plant Pat. No. 20,325) and as its pollen parent the variety known as 'ORAfantanov' (U.S. Plant Pat. No. 23,158).

SUMMARY OF THE INVENTION

Among the features which distinguish the new variety from other presently available and commercial rose cultivars known to the inventor are the following combinations of characteristics: its strong fruity to citrus-like fragrance, its unusual magenta-purple with white reverse flower coloration, its large cluster composed of many flowers and its numerous fine hairs on the upper surface of the young leaves. The plant has a bushy upright moderately spreading to somewhat arching growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKblufstow' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'PEJamblu' by the following combination of characteristics: whereas 'WEKblufstow' bears very double flowers (about 29 to 82 petals) of magenta-purple with white reverse coloration, 'PEJamblu' bears semi-double flowers of mauve/lilac coloration ageing to slate blue with significantly lesser petalage (about 13 to 26 petals). The new variety has a bushy upright moderately spreading to somewhat arching medium height to somewhat tall growing habit (about 100 to about 160 cm. in height), whereas the seed parent has a compact upright shorter growing habit (about 90 to about 120 cm. in height).

The new variety may be distinguished from its pollen parent, 'ORAfantanov' by the following combination of characteristics: whereas 'WEKblufstow' bears very double flowers (about 29 to 82 petals) of magenta-purple with white reverse coloration, 'ORAfantanov' bears semi-double flowers of smoky purple magenta blend coloration with significantly lesser petalage (about 13 to 16 petals). The new variety has a strong fruity to citrus-like fragrance, whereas the pollen parent has strong clove to spicy fragrance.

COMPARISON WITH THE CLOSEST COMMERCIALLY AVAILABLE CULTIVAR

The new variety may be distinguished from its closest commercially available cultivar, 'TEXmourug' (not patented) by the following combination of characteristics: whereas 'WEKblufstow' bears very double flowers (about 29 to 82 petals) of magenta-purple with white reverse coloration, 'TEXmourug' bears double flowers of lavender tones blended with a reverse of creamy white coloration with lesser petalage (about 26 to 40 petals). The new variety is classified as a Shrub rose with a bushy upright moderately spreading to somewhat arching medium height to somewhat tall growing habit (about 100 to about 160 cm. in height), whereas the closest commercially available cultivar is classified as a Climbing rose with a spreading climbing significantly taller growing habit (about 244 to about 305 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

FLOWER

The new variety usually bears its flowers in clusters of four to twenty-nine or more per stem. Flowers are borne in regular rounded clusters on strong medium to long stems (about 28 to about 130 cm.). The cluster ranges from about 11.4 to about 20.2 cm. in diameter. Outdoors, the plant blooms abundantly and nearly continuously during the growing season. The flowers have a strong fruity to citrus-like fragrance.

BUD

The peduncle is about 1.3 to about 6.2 cm. in length, of average caliper (about 0.2 to about 0.4 cm. in diameter), and usually erect. It is moderately rough, with many stipitate glands, and very few hairs. Peduncle color is between 146D and 147C often heavily suffused, especially on the side exposed to the sun, with between 183B and 187A.

Before the calyx breaks, the bud is about 0.9 to about 1.8 cm. in diameter at the widest point, about 0.9 to about 1.8 cm. in length, and pointed to somewhat ovoid in shape. The surface of the bud bears between 2 to 5 foliaceous appendages with many stipitate glands and numerous hairs, usually with slender entire foliaceous parts extending beyond the tip of the bud about ¾ or more of its length. Bud color is between 137C and 147B often heavily suffused, especially on the side exposed to the sun, with between 187B and 187A.

The sepals are 5 per flower, about 1.3 to about 3.3 cm. in length and about 0.5 to about 1.2 cm. in width at the widest point. The outer surface color of the sepal is between 137C and 147B often heavily suffused, especially on the side exposed to the sun, with between 187B and 187A. The outer surface of the sepal is somewhat rough and bears between 0 to 3 foliaceous appendages with many stipitate glands and numerous hairs. The inner surface color of the sepal is near 146C broadly bordered by near 137C. After the sepals open, the inner surface color is often moderately suffused, especially on the area exposed to the sun, with near 187D to as dark as between 187B and 187A. The inner surface of the sepal is covered with fine wooly tomentum; sepal margins are entire and lined with some stipitate glands and numerous hairs. The sepals are permanent, and usually straight in shape with acute apices.

The receptacle of the flower is of medium length (about 0.3 to about 0.7 cm.) and average in caliper (about 0.4 to about 0.9 cm. in diameter). The receptacle is urn-shaped in form. Its surface is mostly smooth with few stipitate glands and with moderately thick fleshy walls. The receptacle color is between 146D and 147C often moderately suffused, especially on the side exposed to the sun, with between 187C and 187D to as dark as 187A.

As the petals open (after the calyx breaks), the bud is about 1.3 to about 2.4 cm. in diameter at the widest point, about 1.5 to about 2.3 cm. in length, and moderately globular to somewhat ovoid in form. The color of the under surfaces of the newly opened petals is between 160C and 155D often heavily suffused on the outermost petals with near 59B to as dark as between 187B and 187A. There is no visible change in coloration at the point where the petal attaches. The color of the upper surfaces of the newly opened petals is between 79B and 71A. At the point where the petal attaches, there is a large zone of between 155A and 155C.

BLOOM

When fully open, the bloom ranges from about 5.5 to about 8.2 cm. in diameter. Petalage is very double with about 29 to 82 petals and about 3 to 32 petaloids irregularly arranged. When partially open, the bloom form is globular to cupped, and the petals are moderately loosely spiraled to cupped with petal edges somewhat reflexed outward. When fully open, the bloom form is cupped, and the petals are loosely cupped with petal edges somewhat reflexed outward. Often some of the intermediate and inner petals are folded along the midrib.

PETALS

The substance of the petals is moderately heavy to somewhat slight and of moderately thin thickness, with upper surfaces moderately satiny and under surfaces slightly shiny. The petals are about 1.7 to about 3.5 cm. in length and about 1.5 to about 4.1 cm. in width at the widest point. Petal margins are entire.

The outer petals are broadly rounded to somewhat obovate in shape with rounded apices and sometimes slightly notched with one notch.

The inner petals are moderately obovate to somewhat oblanceolate in shape with rounded apices and sometimes slightly notched with one notch.

Petaloids are about 0.7 to about 2.6 cm. in length and about 0.4 to about 1.8 cm. in width at the widest point.

Petaloids are irregularly shaped moderately obovate to oblanceolate to somewhat subulate with rounded to sometimes lacerated apices.

NEWLY OPENED FLOWER

The under-surface color of the outer, intermediate and inner petals is between 155C and 155B. There is no visible change in coloration at the point where the petal attaches. The upper surface color of the outer, intermediate and inner petals is between 79B and 71A sometimes edged with between 80A and 74A. At the point where the petal attaches, there is a large zone of between 155A and 155C.

The under and upper surface colors of the petaloids are similar in coloration to the upper and under surfaces of the intermediate and inner petals.

The general tonality of the newly opened flower is between 79B and 71A.

THREE-DAY-OLD FLOWER

The under-surface color of the outer, intermediate and inner petals is between 155C and 155B. There is no visible change in coloration at the point where the petal attaches. The upper surface color of the outer, intermediate and inner petals is between 79D and 71A sometimes edged with between 80A and 74A. At the point where the petal attaches, there is a large zone of between 155A and 155C.

The under and upper surface colors of the petaloids are similar in coloration to the upper and under surfaces of the intermediate and inner petals.

The general tonality of the three-day-old flower is between 79D and 71A.

On the spent bloom, the petals usually drop off.

In November in Wasco, California, blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 25) and are arranged regularly about the pistils; some are mixed with petaloids or tucked in the calyx. The filaments are of somewhat short to medium length (about 0.3 to about 0.7 cm.) most with anthers. Filaments are between 3D and 1D in color. The anthers are somewhat large for the class and all open approximately at the same time. Anther color when immature is near 18B on the external part and near 22A on the internal part. Anther color at maturity is near 175A on the external part and near 202A on the internal part. Pollen is moderate and between 11C and 10D in color.

FEMALE REPRODUCTIVE ORGANS

Pistils vary in number (average about 50). The styles are moderately even, somewhat short to average in length (about 0.3 to about 1.0 cm.), average in caliper, and loosely bunched. Stigma color is between 154C and 1C. Style color is between 155A and 155C. Ovaries are usually all enclosed in the calyx. The ovaries are of medium size and between 158B and 158A in color.

Hips have not been observed on this variety when grown in Wasco, California.

FOLIAGE

The compound leaves are usually comprised of three to seven leaflets and are borne abundantly. The seven-leaflet leaves are about 14.5 to about 21.5 cm. in length and about 9.6 to about 14.5 cm. in width at the widest point, moderately leathery to somewhat crisp in texture on both sides, and glossy in finish on the upper side and slightly glossy in finish on the underside. The leaves have a pinnate venation pattern. The terminal leaflets are about 6.2 to about 9.2 cm. in length and about 3.4 to about 6.0 cm. in width at the widest point, shaped ovate with acute apices and rounded bases. Their margins are usually simply serrate.

The upper surface color of the mature leaf is between 139A and 147A. The under-surface color of the mature leaf is between 147B and 148B. The under and upper colors of the leaf veins on the mature leaf are similar in coloration to the upper and under surfaces colors of the mature leaf. The upper surface color of the young leaf is between 137C and 138A, often heavily suffused with between 187B and 187A. The upper surface of the young leaves is covered with numerous fine hairs. The under-surface color of the young leaf is between 147B and 148B, often heavily suffused with between 187B and 187A. The under and upper colors of the leaf veins on the young leaf are similar in coloration to the upper and under surfaces colors of the young leaf.

The rachis is about 5.5 to about 8.4 cm. in length, about 0.2 to about 0.3 cm in width at the widest point, and rough. The upper side is somewhat shallowly grooved with numerous hairs and very few stipitate glands on the edges of the grooves. The under side of the rachis is rough with some hairs, few stipitate glands and small prickles. The rachis color is near 146D on the underside and near 137C on the upper side, often moderately suffused on the young leaves with between 187B and 187A.

The stipules are about 1.6 to about 2.9 cm. in length and of medium width to somewhat wide (about 0.4 to about 0.9 cm.) with long straight points that usually turn out at an angle of more than 45 degrees. The under and upper surface color of the stipule is between 139A and 137A sometimes moderately suffused on the young leaves with between 187C and 187A. The upper and under surfaces of the stipules are smooth in texture.

The petiole is average to somewhat heavy in caliper and rough. The upper side is somewhat shallowly grooved with numerous hairs and very few stipitate glands on the edges of the grooves. The under side of the petiole is rough with some hairs, few stipitate glands and small prickles. The petiole is about 0.8 to about 2.7 cm. in length and about 0.2 to about 0.3 cm in width at the widest point. The petiole color is near 146D on the underside and near 137C on the upper side, often moderately suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, California. The plant's winter hardiness and drought/heat tolerance are yet to be determined.

GROWTH

The plant has a bushy upright moderately spreading to somewhat arching medium height to somewhat tall growing habit (about 100 to about 160 cm. in height and about 96 to about 150 cm. spread at the widest point), with full branching. It displays vigorous growth and the canes are of somewhat light to medium caliper for the class (about 1.2 to about 1.7 cm. in diameter at the widest point).

The color of the major stems is between 146A and 147B. The major stems are rough in texture and they bear few large prickles that are about 0.4 to about 0.9 cm. in length. The large prickles are angled moderately downward with a long narrow oval base; prickle color is between 164A and 165B often moderately suffused with near 201D. The major stem bears some small prickles of similar shape and coloration.

The color of the branches is between 146B and 146A. The branches are rough in texture and they bear few large prickles which are of similar size and shape to the large prickles on the major stems; prickle color is between 163C and 162A usually moderately suffused with between 187C and 187D. The branches bear several small prickles of similar shape and coloration with many stipitate glands and few hairs.

The color of the new shoots is between 146B and 146C often moderately suffused with between 187C and 187B. The new shoots are rough in texture and they bear some large prickles which are of similar size and shape to the large prickles on the major stems; prickle color is near 162A usually heavily suffused with between 187B and 187C. The shoots bear several small prickles of similar shape and coloration with many stipitate glands and few hairs.

I claim:

1. A new and distinct Shrub rose plant of the variety designated 'WEKblufstow' substantially as described and illustrated herein.

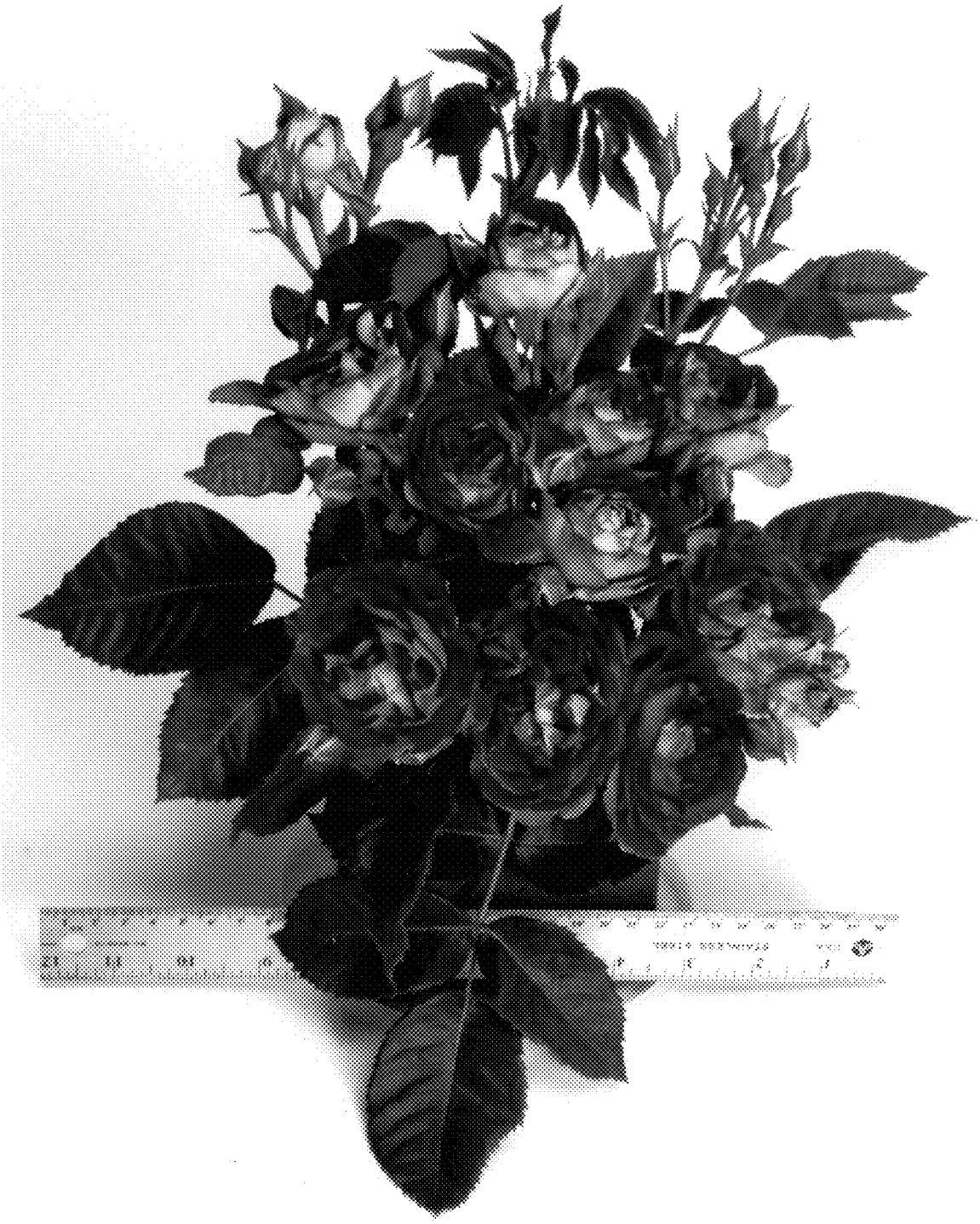

* * * * *